US00PP27990P3

(12) United States Plant Patent
Klemm et al.

(10) Patent No.: US PP27,990 P3
(45) Date of Patent: May 9, 2017

(54) ***FUCHSIA* PLANT NAMED 'KLEFU14838'**

(50) Latin Name: ***Fuchsia* sp.**
Varietal Denomination: KLEFU14838

(71) Applicant: Klemm+Sohn GmbH & Co. KG, Stuttgart (DE)

(72) Inventors: Nils Klemm, Stuttgart (DE); Andrea Dohm, Pforzheim (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 156 days.

(21) Appl. No.: 14/545,973

(22) Filed: Jul. 13, 2015

(65) Prior Publication Data
US 2017/0020048 P1 Jan. 19, 2017

(51) Int. Cl.
*A01H 5/02* (2006.01)

(52) U.S. Cl.
USPC ..... Plt./300

(58) Field of Classification Search
USPC ..... Plt./263.1, 300
See application file for complete search history.

*Primary Examiner* — Susan McCormick Ewoldt
*Assistant Examiner* — Karen Redden
(74) *Attorney, Agent, or Firm* — Barbara Campbell; Bethany R. Roahrig; Cochran Freund & Young, LLC

(57) ABSTRACT

A new *Fuchsia* plant particularly distinguished by having a compact, upright plant habit with small flowers, is disclosed.

1 Drawing Sheet

Genus and species: *Fuchsia* sp.
Variety denomination: 'KLEFU14838'.

BACKGROUND OF THE NEW PLANT

The present invention comprises a new and distinct variety of *Fuchsia*, botanically known as *Fuchsia* sp. and hereinafter referred to by the variety name 'KLEFU14838'. 'KLEFU14838' is a selection from a controlled cross-pollination of the proprietary female *Fuchsia* line '2010.5' (unpatented) and the proprietary male *Fuchsia* line '2010.11' (unpatented).

In March of 2011, the proprietary female *Fuchsia* line '2010.5' and the proprietary male *Fuchsia* line '2010.11' were cross pollinated in Stuttgart, Germany and seeds were obtained. The seeds were sown and plants were grown for evaluation. A plant line was selected in March 2012 in Stuttgart, Germany and named 'KLEFU14838'. In March 2012, 'KLEFU14838' was first vegetatively propagated by in Stuttgart, Germany via vegetative cuttings. 'KLEFU14838' was found to reproduce true to type in successive generations of asexual propagation via vegetative cuttings in Stuttgart, Germany.

SUMMARY

The following are the most outstanding and distinguishing characteristics of this new variety when grown under normal horticultural practices in Stuttgart, Germany.

1. Compact, upright plant habit; and
2. Small flowers.

DESCRIPTION OF THE PHOTOGRAPH

This new *Fuchsia* plant is illustrated by the accompanying photograph, which shows a close-up of the flower of the plant. The plant is about 3 months-old grown in Stuttgart, Germany in May 2014. The colors shown are as true as can be reasonably obtained by conventional photographic procedures.

DESCRIPTION OF THE NEW VARIETY

The following detailed descriptions set forth the distinctive characteristics of 'KLEFU14838'. The data, which define these characteristics, were collected from asexual reproductions carried out in Latina, Italy. Data was collected on 2.5 to 3 month-old plants in Latina, Italy in June 2015. Color references are to The R.H.S. Colour Chart of The Royal Horticultural Society of London (R.H.S.), 5$^{th}$ edition (2007).

Classification:
- *Family.*—Onagraceae.
- *Classification.*—*Fuchsia* sp.
- *Common name.*—*Fuchsia.*

Propagation:
- *Type.*—Vegetative cuttings.
- *Time to initiate roots, summer.*—About 1 to 2 weeks at 20° C. to 25° C.
- *Time to initiate roots, winter.*—About 2 weeks at temperatures of 18° C. to 22° C.
- *Time to produce a rooted young plant, summer.*—3 to 4 weeks at temperatures of 20° C. to 25° C.
- *Time to produce a rooted young plant, winter.*—4 weeks at temperatures of 18° C. to 22° C.
- *Root description.*—Fine, fibrous, yellowish-white in color.
- *Rooting habit.*—Freely branching; medium density.

Plant description:
- *Plant habit.*—Compact, upright plant habit.
- *Growth habit.*—Freely branching habit with lateral branches developing potentially at every node; bushy plant habit; vigorous growth habit.
- *Plant height.*—20.0 cm to 22.0 cm.
- *Plant diameter.*—25.0 cm to 28.0 cm.

Lateral branch description:
*Length*.—Approximately 15.0 cm to 18.0 cm.
*Diameter*.—Approximately 2.0 mm.
*Internode length*.—Approximately 2.8 cm.
*Strength*.—Strong, flexible.
*Aspect*.—Initially upright to semi-upright, compact.
*Texture*.—Pubescent.
*Color*.—Close to RHS 146B lightly tinted with close to RHS 187A.

Foliage description:
*Arrangement*.—Opposite, simple.
*Length*.—2.8 cm to 3.8 cm.
*Width*.—1.4 cm to 1.8 cm.
*Shape*.—Ovate.
*Apex*.—Broadly acute.
*Base*.—Obtuse and rounded.
*Margin*.—Shallowly serrate.
*Texture*.—Upper and lower surfaces: Glabrous.
*Venation pattern*.—Pinnate; arcuate.
*Venation color*.—Upper surface: Close to RHS 146B, occasionally lightly tinted with close to RHS 183A. Lower surface: Close to RHS 147B, occasionally lightly tinted with close to RHS 183A.
*Color*.—Developing leaves: Upper surface: Close to RHS N137C. Lower surface: Close to RHS 137B. Fully expanded leaves: Upper surface: Close to RHS N137A. Lower surface: Close to RHS 147A.

Petiole:
*Length*.—Approximately 0.9 cm.
*Diameter*.—Approximately 1.8 mm.
*Texture*.—Smooth, glabrous. Upper surface: Smooth, glabrous, concave. Lower surface: Smooth, glabrous, convex.
*Color*.—Upper surface: Close to RHS 146B, occasionally lightly tinted with close to RHS 183A. Lower surface: Close to RHS 147B, occasionally lightly tinted with close to RHS 183A.

Flower description:
*Flower arrangement and habit*.—Single axillary flowers; flowers pendulous; freely flowering habit with potentially two flowers per leaf axil.
*Total number of flowers per plant*.—Over 40 fully open flowers and 80 buds on a mature plant when at flowering stage.
*Fragrance*.—None detected.
*Natural flowering season*.—Long flowering period; in Europe, plants flower from early spring to autumn; flowering continuous during this period.
*Flower longevity*.—Flowers last about four to six days on the plant.
*Flower diameter*.—0.9 cm (petals), 5.1 cm (sepals).
*Flower height* (*depth*).—Approximately 4.8 cm (base of sepals to stigma tip).
*Flower buds*.—Shape: Elliptic. Length: Approximately 2.7 cm. Diameter: Approximately 1.1 cm. Color: RHS 45A.

Petals:
*Arrangement*.—Typically four in a single whorl.
*Length*.—Approximately 1.8 cm.
*Width*.—Approximately 1.3 cm.
*Shape*.—Obovate.
*Apex*.—Obtuse.
*Base*.—Cuneate.
*Margin*.—Entire.
*Texture*.—Glabrous, all surfaces. Upper and lower surface: Smooth, glabrous; satiny.
*Color*.—Upper (outside) surface: When opening: RHS N83A. Fully open: RHS N77A. Lower (inside) surface: When opening: RHS N83B. Fully open: RHS N77A.

Sepals:
*Arrangement*.—Calyx star-shaped with four sepals fused at the base.
*Length*.—2.6 cm.
*Width*.—0.8 cm.
*Shape*.—Elliptic.
*Apex*.—Slightly cuspidate.
*Base*.—Attenuate, fused.
*Margin*.—Entire.
*Texture*.—Upper (outside) and lower (inside) surfaces: Smooth, glabrous; satiny.
*Color*.—Upper (outside) surface: When opening: RHS 45A. Fully opened RHS 45B. Lower (inside) surface: When opening: RHS 45B. Fully opened: RHS 45D.

Peduncles:
*Length*.—1.2 cm to 3.5 cm.
*Diameter*.—0.08 cm to 0.1 cm.
*Angle*.—Arching.
*Strength*.—Moderately strong.
*Texture*.—Sparsely pubescent.
*Color*.—Close RHS 144A.

Reproductive organs:
*Stamens*.—Quantity: 8. Anther shape: Ellipsoidal. Anther size: About 2.0 mm by 1.0 mm. Anther color: RHS 158A with Red-Purple RHS N57B shading. Pollen amount: Moderate. Pollen color: Close to RHS 155A.
*Pistils*.—Quantity: 1 per flower. Pistil length: 5.0 cm. Style color: towards the base, close to RHS 155D; towards the apex, close to RHS 54A. Stigma shape: Clavate. Stigma color: RHS 49A. Ovary color: RHS 144A.

Seeds and fruits: No fruit or seed observed.

Disease and insect resistance: No disease or insect resistance observed.

COMPARISON WITH PARENTAL LINES AND KNOWN VARIETY

'KLEFU14838' is a distinct variety of *Fuchsia*. 'KLEFU14838' is distinguished from its parents as described in Table 1:

TABLE 1

Comparison with Parental Lines

| Trait | Variety 'KLEFU14838' | Female parent '2010.5' | Male Parent '2010.11' |
|---|---|---|---|
| Plant height | Short | Medium | Medium |
| Flower size | Small | Medium | Medium |

'KLEFU14838' is most similar to the commercial *Fuchsia* plant 'Kiecandipu', commercially known as Diva Rose Purple (U.S. Plant Pat. No. 15,338). Differences between the two varieties are described in Table 2:

TABLE 2

Comparison with Similar Variety

| Characteristic | Variety 'KLEFU14838' | Commercial line 'Kiecandipu' |
|---|---|---|
| Plant height | Short | Medium |

We claim:

1. A new and distinct variety of *Fuchsia* plant named 'KLEFU14838' as illustrated and described herein.

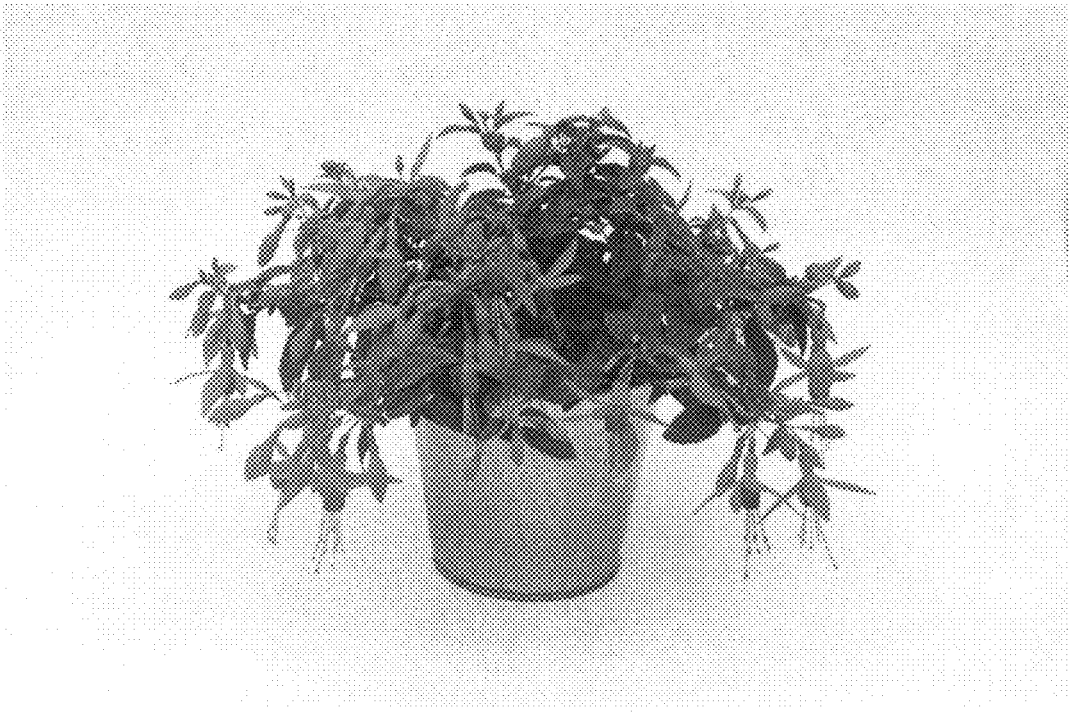

* * * * *